United States Patent [19]

Kuhrts

[11] Patent Number: 4,965,252

[45] Date of Patent: Oct. 23, 1990

[54] CHOLESTEROL-LOWERING COMBINATION COMPOSITIONS OF GUAR GUM AND NIACIN

[75] Inventor: Eric H. Kuhrts, Santa Barbara, Calif.

[73] Assignee: Hauser-Kuhrts, Inc., Santa Barbara, Calif.

[21] Appl. No.: 212,715

[22] Filed: Jun. 28, 1988

[51] Int. Cl.$^5$ .................... A61K 31/33; A61K 31/715
[52] U.S. Cl. ........................ 514/54; 514/188; 514/183; 514/911; 514/951; 514/909; 536/114; 536/123
[58] Field of Search ................ 514/54, 188, 183, 911, 514/951, 909; 536/123, 114

[56] References Cited

PUBLICATIONS

Drug Facts and Comparisons, 1988, p. 19, Plus Cover Sheet.

*Primary Examiner*—Ronald W. Griffin
*Assistant Examiner*—Pamela S. Webber
*Attorney, Agent, or Firm*—Gordon W. Hueschen

[57] ABSTRACT

An antihyperlipidemic pharmaceutical or dietary supplement composition for oral use consisting essentially of a combination of niacin and guar gum, and a method of lowering cholesterol levels with such oral pharmaceutical composition, or by the simultaneous oral administration of the active ingredients thereof, which eliminates the usual undesirable flushing and itching side effects of niacin while effectively lowering cholesterol levels, especially LDL cholesterol levels, is disclosed.

31 Claims, No Drawings

CHOLESTEROL-LOWERING COMBINATION COMPOSITIONS OF GUAR GUM AND NIACIN

BACKGROUND OF THE INVENTION

1. Field of Invention

Antihyperlipidemic pharmaceutical or dietary supplement compositions and method of treating hyperlipidemic conditions therewith; combination compositions and therapy employing niacin and another active antihyperlipidemic principle, namely, guar gum, which eliminate the usual undesirable side effects of niacin.

2. Background of the Invention and Prior Art

Nicotinic acid was the only agent studied by the Coronary Drug Project which produced a significant decrease in coronary events. Coronary Drug Project Research Group: Clofibrate and Niacin and Coronary Heart Disease. JAMA 231:360 (1975). This research demonstrated that niacin lowers blood cholesterol on an average by nine percent and reduces the recurrence rate of myocardial infarction by 29%. The study involved more than 8,000 individuals and was conducted over a period of six (6) years. The usual dosage range for niacin therapy is 3 to 6 grams per day, which dosage is capable of lowering cholesterol level from 10 to 25%, triglyceride level by 45 to 50%, and elevating HDL cholesterol by 15 to 20%.

In a paper in the Journal of Lipid Research 22:24–36 (1981) entitled "Influence of Nicotinic Acid on Metabolism of Cholesterol and Triglycerides in Man", it is stated as follows:

"Although the magnitude of plasma lipid lowering by nicotinic acid can be appreciable, its usefulness has been limited by certain disagreeable side effects such as flushing of the face and other skin reactions."

Although the actual mechanisms by which niacin reduces cholesterol and triglycerides is not completely known, it is known that niacin does produce these effects and that niacin, moreover, has an ability to increase the amount of the protective form of cholesterol, namely, HDL cholesterol.

A major shortcoming of niacin is the necessity of administering large doses of niacin to effectively lower cholesterol level. Most subjects treated will experience accompanying side effects of flushing, prickling of the skin, and itching when they begin niacin, when the dosage is increased, or when the treatment is temporarily terminated and then commenced once more at the same dose. Ordinarily, it is necessary for a subject to gradually increase the dosage of niacin to a three to six gram per day dosage level over a period of months, starting with one 50 mg tablet three times daily for a total dose of 150 mg per day, to avoid being overwhelmed with the unpleasant side effects.

The prior art is replete with reports of the reduction of cholesterol levels and control of cholesterol levels in a subject in need of the same employing niacin (nicotinic acid) and of the undesirable side effects ordinarily produced when an effective amount of niacin is employed for such purpose. The side effects include flushing and itching, and it is well documented in the literature that such flushing, itching, and so on is not eliminated by intermittent niacin therapy, and generally reappears even when the therapy is interrupted and reinstituted. Although the degree or intensity of such side effects varies from patient to patient, it is frequently observed that such therapy cannot be applied in the case of various patients who are hypersensitive to the niacin or to the side effects which result in such patients upon oral administration thereof.

Numerous other approaches to the lowering of cholesterol in a subject in need thereof have been proposed. For example, cholestyramine and other drugs which theoretically affect the bile acid pool and pull cholesterol out of the bloodstream according to the postulated mechanism are also available as are the dietary fiber materials, such as guar gum and the like. Guar gum has been suggested as a dietary supplement fiber having an effect on cholesterol upon ingestion, but having a somewhat reduced effect when compared to bile acid-binding agents such as cholestyramine. Although the effect of guar gum is clear, its mechanism of action as a plasma cholesterol-lowering agent is unclear. What is clear, however, is that guar gum has no specific affinity for either cholesterol or for bile salts and that it does not act as a bile acidbinding agent in the manner of cholestyramine or the like, being 60–70 percent less effective in this regard, but yet being able to lower cholesterol levels almost as well as cholestyramine.

Dietary supplements or regimens combining oat bran and niacin have been recommended, but there has been no evidence or suggestion that such combination dietary treatment or approach has any effect upon the undesirable side effects of niacin, least of all at cholesterol-lowering dosages or intakes. Although it has been reported that side effects and especially gastric irritation may be somewhat reduced by taking the medication with meals and by the use of antacids or by combined therapy with colestipol, a bile acidsequestering resin having proton-binding properties, its side effects continue to hamper its general applicability in cholesterol lowering and poor patient compliance often results because of these side effects.

It is accordingly reported that "Continuous flushing, resulting from harmless dilation of skin capillaries, occurs in most individuals at onset of treatment and when dosage is increased. Patients should be warned that if several doses are missed, the flushing will recur. Gastric irritation is also frequently encountered.

Since niacin, at a dosage level of three to six grams per day, is very effective in reduction of undesirable cholesterol levels, which reportedly fall by a mean of approximately 22% during some controlled clinical evaluations, it would be highly desirable to provide a way in which this valuable cholesterollowering material could be more generally applied without fear of or limitation by the said undesirable side effects, and the present invention addresses this problem, which has heretofore had no satisfactory solution, by combined therapy employing also guar gum, a natural fiber which itself is a dietary supplement known to produce cholesterol-lowering effect, but which unpredictably, as found according to the present invention, essentially eliminates or at least very substantially reduces the usual niacin side effects when administered simultaneously and preferably in a combination composition therewith.

Combination therapy employing colestipol, a bile acid sequestrant, together with niacin or its prodrug clofibrate, produced reduction in cholesterol levels as expected, which were greater when niacin was used together with colestipol rather than its prodrug clofibrate, but care still had to be taken to "mitigate the prostaglandin-mediated cutaneous flushing often associated with niacin", aspirin therefore being administered a half hour before each dose of niacin for this purpose. Combination therapy involving Lovastatin, plus a resin such as cholestyramine or colestipol, and niacin has also been suggested, it being reported that the Lovastatin reduced the amount of resin and niacin required to produce satisfactory results, and providing a possible powerful therapy for severe familial hypercholesterolemia, although such bile acid-sequestering resins are suspect as possibly binding and at least partially inactiviting niacin as well. In any case, the combination of niacin plus the already-established guar gum fibrous dietary supplement (fiber intake already having been established as "inversely related to all-cause mortality"), as provided by the present invention, would appear to be a much simpler solution to the problem of the undesirable niacin side effects, while at the same time providing effective doublebarrel cholesterol-lowering effect and results, than any combination, method-of-treating, or dietary supplement approach which has been suggested previously.

Guar gum is derived from a leguminous plant which bears bean-like pods containing six to nine seeds, known as Cyanopsis tetragonoloba. The seed is 40–46% germ, 38–45% endosperm, and 14–16% husk. Guar gum is prepared by first removing the husk and sperm components and then is derived essentially from the endosperm. It is marketed commercially in different grades and is chemically a galactomannan with galactose on every other mannose unit, having a molecular weight of approximately 220,000. It disperses in cold water to form a viscous pseudoplastic sol, the viscosity of which can be enhanced with heating, and it has an extremely high viscosity, which is fivefold higher per unit weight than starch, and is commercially available in various grades of dispersibility, viscosity, and thickening power, being generally packaged in powder form which requires dispersion in water. The problem of dispersing the guar gum in water is one which confronts one desiring to prepare a drinkable dispersion thereof, and also one who desires to disperse the guar gum internally upon oral ingestion, especially when most rapid action is desired. Although the mechanism of action as a plasma cholesterol-lowering agent of guar gum is unclear, it is clear that both niacin (nicotinic acid) and guar gum have been known to be effective cholesterol-lowering entities for at least twenty (20) years but, up to the time of this invention, no one has disclosed or even suggested that a combination of guar gum and niacin would virtually eliminate the unpleasant and normally limiting side effects of niacin in addition to providing enhanced cholesterollowering effect.

A Dialog search from the U.S. Patents data base for niacin for U.S. Pat. Abstracts No. 1971–81, 1982–1987, and weekly from 12/87 through the middle of Feb. 1988, turned up a few niacin prodrugs with or without allegedly reduced side effects and U.S. Pat. No. 4,166,902 relating to high polymers containing nicotinic acid in which nicotinic acid radicals are bound through covalent ester bonds which gradually hydrolyze in a biological environment by setting free nicotinic acid, and which allegedly have a therapeutic activity similar to that of nicotinic acid itself but longer lasting and with the elimination or least reduction of "collateral effects", the product of this patent apparently being some sort of a "depo" nicotinic acid-containing material, but of course the question remains whether the slow release of nicotinic acid as disclosed in this patent will provide adequate niacin levels for effective cholesterol lowering in practice. At any rate, this patent merely emphasizes the continued existence of the problem of niacin side effects and allegedly provides one approach to its possible solution, being in no way suggestive of the entirely different solution to the problem discovered by the present applicant.

OBJECTS OF THE INVENTION

It is an object of the present invention to provide a method of lowering cholesterol, especially LDL cholesterol, in a subject in need of the same, by the employment of nicotinic acid (niacin) in combination with guar gum, which is highly effective for its intended purpose and which has the further advantageous and unpredictable effect of eliminating or substantially reducing the usual flushing and related side effects of niacin. A further object of the invention is the provision of such a method wherein the niacin and the guar gum are administered simultaneously. An additional object of the invention is the provision of a combination composition comprising both niacin and guar gum which is useful for the aforesaid purpose. A still further object of the invention is the provision of such a method wherein a soluble mineral salt, especially a physiologically-acceptable soluble magnesium salt, is also administered simultaneously with the active ingredients niacin and guar gum, and a combination composition of the active ingredients niacin and guar gum comprising also the soluble, e.g., magnesium, salt. Still a further object of the present invention is the provision of such a method and such a combination composition which may be employed in the reduction of cholesterol levels either as or as a part of a medical or a pharmaceutical regimen or therapy for the reduction of cholesterol levels in a subject in need of the same, or as a food supplement for the effective reduction of cholesterol levels in a subject in need of the same according to the current practice of providing guar gum or other fibrous material according t good-health dietary practices for or by a subject desiring to reduce cholesterol levels to or maintain the same at levels which are considered to be acceptable and/or relatively safe from a dietary or medical standpoint. Further objects of the invention will become apparent hereinafter, and still others will be obvious to one skilled in the art to which this invention pertains.

SUMMARY OF THE INVENTION

In summary then, the present invention comprises, inter alia, the following, singly or in combination:

An oral antihyperlipidemic composition of nicotinic acid characterized by reduced flushing effect comprising as active ingredients nicotinic acid and guar gum; such a composition wherein the composition contains at least about 50 mg of nicotinic acid; such a composition wherein the amount of nicotinic acid is at least about 50 mg and the amount of guar gum is at least about 250 mg; such a composition wherein the amount of nicotinic acid is at least about 50 mg and the amount of guar gum is at least about 400 mg, in capsule or tablet form; such a composition wherein the amount of nicotinic acid is at least about 50 mg and the amount of guar gum is at least about 400 mg, comprising also an antacid; such a composition comprising a physiologically-acceptable magnesium salt; such a composition comprising an orally-ingestible non-toxic mineral salt capable of dissolution in the gastric fluid; such a composition wherein the mineral salt is selected from the group consisting of calcium carbonate, magnesium carbonate, and potassium carbonate; such a composition wherein the active ingredients are in powder form and comprising also a quantity of a food-grad acid in powder form which is effective in extending the time for gelation of the resulting mix upon addition of water; such a composition wherein the food-grade acid is selected from the group consisting of citric acid, ascorbic acid, tartaric acid, and malic acid; and such a composition comprising about 400–500 mg guar gum, about 80–100 mg niacin, and about 80–100 mg magnesium carbonate.

Moreover, a method of combating hyperlipidemia in a subject in need of the same using nicotinic acid characterized by reduced flushing effect comprising the step of simultaneously administering orally to the said subject both nicotinic acid and guar gum; such a method comprising the step of administering orally to the said subject both nicotinic acid and guar gum in the form of a pharmaceutical composition containing both active ingredients; such a method comprising the step of administering orally to the said subject both nicotinic acid and guar gum in the form of a pharmaceutical composition containing both active ingredients in capsule or tablet form; such a method comprising the step of administering orally to the said subject both nicotinic acid and guar gum in the form of a pharmaceutical composition containing both active ingredients in capsule or tablet form comprising also an antacid; such a method wherein a single dosage comprises about 300–500 mg of niacin and about 1.5–2.5 g of guar gum; such a method wherein a single dosage comprises about 300–500 mg niacin, about 1.5–2.5 g of guar gum, and about 300–500 mg of a physiologically-acceptable magnesium salt; such a method wherein a dosage unit comprises at least about 250 mg guar gum and at least about 50 mg niacin; such a method wherein a single dose comprises at least about 2 g guar gum and at least about 350 mg of niacin; such a method wherein a daily dose comprises at least about 6 g guar gum, at least about 1 g niacin, and at least about 1 g magnesium carbonate; such a method wherein an orallyingestible non-toxic mineral salt capable of dissolution in the gastric fluid is simultaneously orally administered; such a method wherein a physiologicallyacceptable magnesium salt is also simultaneously orally administered; such a method wherein the physiologicallyacceptable magnesium salt is magnesium carbonate; such a method wherein the active ingredients are in powder form and wherein a quantity of a food-grade acid also in powder form which is effective in extending the time for gelation of the resulting mix upon addition of water is also simultaneously orally administered, and such a method wherein the mineral salt is selected from the group consisting of calcium carbonate, magnesium carbonate, and potassium carbonate.

GENERAL DESCRIPTION OF THE INVENTION

The invention, in general, is set forth under "Objects of the Invention" and "Summary of the Invention" but, in short, comprises the combination with niacin of guar gum, both of which are known to be effective antihypercholesterolemic agents, with the resulting effect that an extremely effective oral antihypercholesterolemic combination is provided, preferably in a single-dosage unit form. Alternatively, the two active ingredients may be orally administered simultaneously; although administration of both together in a combination composition is preferred. In addition to the desired and augmented antihypercholesterolemic effect of the combination and combination therapy of the present invention, the usual cutaneous flushing, resulting in itching or prickling of the skin, as well as bright-red blushing, which ordinarily results from harmless dilation of the skin capillaries in the course of niacin therapy and which frequently manifests itself even at a niacin dose as low as 50 mg, has unpredictably been found to be greatly reduced or essentially eliminated when the niacin is administered or ingested in combination with the guar gum, the ratio of the guar gum fibers to the nicotinic acid preferably being approximately five parts of fiber to one part of nicotinic acid on a weight basis, although broader ranges are of course effective. Advantageously, a metal salt which is soluble in the gastro-intestinal fluids is provided as a buffer or to enhance dispersability of the guar gum. Morever, the inclusion of a magnesium salt which is soluble in the gastro-intestinal fluids also appears to reduce still further the flushing, itching, and other usual side effects of the niacin therapy, and is accordingly preferred. The exact form in which the active ingredients are orally administered is not important, so long as the objectives of the invention are obtained. The active ingredients may take the form of the usual tablets, capsules, suspensions, dispersions, elixirs, syrups, or the like, whether administered singly or in combination, and may moreover be provided in the usual form for dietary supplements involving inclusion of a fibrous material, such as in capsules, drink mixes, breakfast foods, or the like, especially when metallic salts assisting with the internal dispersion of the guar gum are included and/or when acids, and especially organic acids such as citric, ascorbic, malic, and tartaric are included not only to delay gelation of the guar gum when the active ingredients are presented in the form of a drink mix but also to add a pleasant palatable flavor thereto.

DETAILED DESCRIPTION OF THE INVENTION

The following Examples are given to illustrate the invention, but are not to be construed as limiting.

EXAMPLE 1

A composition is prepared according to the following formula:

Guar gum (Cyamopsis Tetragonoloba) 400–500 mg
Niacin (nicotinic acid) 80–100 mg

These ingredients, guar gum and niacin, are blended together and encapsulated in a hard gelatine capsule. A lubricating agent may as usual be used to facilitate encapsulation. This formula can be conveniently orally ingested at an effective therapeutic dose of five (5) capsules, preferably three (3) times a day.

At a dosage of five (5) capsules, the amount of active ingredients is 2,000–2,500 mg of guar gum and 400–500 mg of niacin, close to the preferred ratio of five parts of fiber to one part of niacin.

When this dosage is taken three (3) times daily, the total amount of guar gum is 6 to 7.5 grams and the amount of niacin is 1.2–1.5 grams, an effective dosage regimen although involving less than the usually recommended daily dose of niacin when used alone.

EXAMPLE 2

In addition to the guar gum and the niacin in the amounts set forth in Example 1, magnesium carbonate is included in the composition in an amount of 80–100 mg per capsule. At a therapeutic dose of five (5) capsules, this makes the amount of magnesium carbonate 400–500 mg and, at a TID regimen, the number of capsules 15 per day, the amount of magnesium carbonate ingested then being 1.2–1.5 grams.

EXAMPLE 3

In additional formulations, calcium carbonate, aluminum hydroxide, or other physiologically-acceptable mineral salt is employed as buffer or antacid.

EXAMPLE 4

A further specific Example of a formulation according to the present invention is the following:

| Guar gum | 470 mg |
|---|---|
| Niacin | 74 mg |
| Magnesium carbonate | 74 mg |

PHARMACOLOGICAL AND CLINICAL EVALUATION

A. The cholesterol-lowering properties of the combination composition of Example 1 are examined clinically at a dosage of five (5) capsules TID, making 15 per day in all, taken at mealtime, over a period of two (2) weeks.

This is equivalent to approximately 7.05 grams of guar gum and 1.11 grams of niacin per day.

The results of the clinical study are as follows:

| Participant | Total Cholesterol Before mg/dl | Total Cholesterol After mg/dl | Difference mg/dl | % Reduction |
|---|---|---|---|---|
| M.T. | 264 | 210 | −54 | 20.5 |
| M.A. | 318 | 256 | −62 | 19.5 |
| K.E. | 262 | 220 | −42 | 12.2 |
| W.J. | 387 | 293 | −94 | 24.3 |
| O.M.M. | 236 | 212 | −24 | 10.2 |

The formulation of the invention greatly reduces the side effects of niacin, such as cutaneous flushing, resulting in itching or prickling of the skin and bright-red blushing, which is a result of the dilation of the skin capillaries and which occurs in most individuals at the beginning of treatment and whenever the dosage is increased.

B. In similar clinical tests using the formulation set forth in Example 2, the results are essentially identical. However, the amount of flushing, itching, prickling, and blushing, as subjectively experienced by the subjects in the test panel themselves and as observed by other members of the test panel, is unpredictably still further reduced. In addition, the amount of gastro-intestinal distress is substantially reduced due to the buffering effect of the magnesium carbonate employed.

C. According to the present invention, a further cholesterol-lowering study is carried out employing the combination compositions of the present invention according to Example 4. In the present study, each participant orally ingests a niacin combination composition according to the present invention having the following formula:
Dose: Five (5) capsules, TID (3 times a day)
Each capsule containing:
74 mg niacin
470 mg guar gum
74 mg magnesium carbonate At a dose of five capsules, the amount of niacin is 370 mg, the amount of guar gum 2.35 g, and the amount of magnesium carbonate is 370 mg. At a dosage regimen of three times per day (TID) the amount of niacin is 1.11 grams, the amount of guar gum is 6.9 grams, and the amount of magnesium carbonate is 1.11 grams.

This dosage produces results equivalent to those set forth under "A", including a reduction in total cholesterol which averages 20.37% in the test panel of five (5) subjects, which is nearly equivalent to the results obtained using a nicotinic acid dosage of three (3) grams per day. In other words, in the present combination, a daily dosage of niacin which amounts to one-third of the daily dose, usually employed for niacin alone, is capable of lowering total cholesterol to approximately the same degree, and without the intolerable side effects ordinarily produced by niacin alone at such dosage levels.

Alternatively, the clinical study can be observed by administering the active ingredients nicotinic acid and guar gum simultaneously. As already pointed out, calcium carbonate or other mineral carbonate can be substituted for the magnesium carbonate, although a magnesium salt such as magnesium carbonate, magnesium oxide, or magnesium hydroxide, but preferably magnesium carbonate, produces unobvious and clear-cut advantages, as already set forth.

In an extension of the clinical evaluation set forth in the foregoing under "C", subject No. 1 after seventeen (17) days and subject No. 2 after eighteen (18) days were evaluated from the standpoint of effect upon different types of blood components, the following cumulative summary report indicating for No. as follows:

|  | Day 1 | Day 17 |  |
|---|---|---|---|
| Cholesterol | 387 | 293 | MG/DL |
| Triglyceride | 357 | 198 | MG/DL |
| HDL-C | 39 | 42 | MG/DL |
| LDL-C | 277 | 211 | MG/DL |
| VLDL-C | 71 | 40 | MG/DL |
| LDL-C/HDL-C | 7.0 | 5.0 |  |
| Chol/HDL-C | 9.9 | 7.0 |  |

With respect to subject No. 2, the following cumulative summary report shows the results after eighteen days according to the suggested five (5) capsule dosage TID using the combination composition of Example 4 hereof.

|  | Day 1 | Day 18 |  |
|---|---|---|---|
| Cholesterol | 264 | 210 | MG/DL |
| Triglyceride | 101 | 70 | MG/DL |
| HDL-C | 53 | 56 | MG/DL |
| LDL-C | 191 | 140 | MG/DL |
| VLDL-C | 20 | 14 | MG/DL |
| LDL-C/HDL-C | 3.6 | 2.5 |  |
| Chol/HDL-C | 5.0 | 3.7 |  |

From the foregoing, it is clear that in both cases the HDL cholesterol percentage was increased while the LDL cholesterol and the VLDL cholesterol was substantially reduced, as well as total cholesterol and triglyceride content, and that the ratios of LDL-C to HDL-C and Chol/HDL-C dropped considerably.

Extremely noteworthy is the improved LDL/HDL ratio, which is indicative of a reduced risk for heart disease according to established interpretation of such results.

According to the practice of the art, the niacin or nicotinic acid may be provided as such or in the form of a prodrug thereof, numerous of which are presently available and which break down, to a greater or lesser extent upon ingestion, to provide nicotinic acid in the system of the subject orally ingesting the same for reduction or control of cholesterol levels in the said subject. Representative prodrugs of this type are derivatives of nicotinic acid, especially esters, and the like, and many of these prodrugs are also subject to the same side effects as niacin itself, namely, the production of the undesirable and sometimes intolerable side effects of flushing, itching, and the like and, to the extent that these prodrugs do provide an effective antihyperipidemic amount of niconitic acid upon ingestion, as well as the undesirable side effects of niacin previously mentioned, they may be employed according to the present invention in lieu of niacin itself, the method and combination compositions of the present invention providing effective cholesterol-lowering effect as well as reduction or essential elimination of the undesirable effects of niacin when such a prodrug is employed just as in the case of the employment of niacin itself.

As already stated, in a particularly preferred embodiment according to the present invention, a physiologically-acceptable soluble magnesium salt is administered simultaneously together with the active ingredients according to the present invention, namely, niacin and guar gum, and most preferably in a combination composition together therewith. The inclusion of the physiologically-acceptable magnesium salt appears to still further reduce the flushing and related side effects of the niacin and such magnesium salt may illustratively but not limitatively be or comprise magnesium carbonate, magnesium chloride, magnesium oxide, magnesium hydroxide, or any other physiologically-acceptable salt of magnesium with either a mineral or organic acid which is soluble, that is, capable of dissolution in the gastric fluids.

According to one preferred embodiment of the present invention, the active ingredients, namely, niacin and guar gum, are provided in granular form for addition to water to provide a drinkable form of oral administration. When employed in this form, a quantity of a food-grade acid, also in powder form, which is effective in extending the time for gelation of the resulting mix upon addition of or to water, is also preferably supplied concurrently or simultaneously with the aforementioned active ingredients and, in the most preferred form, is provided in the form of a granular mix together with the other active ingredients so as to provide a combination granular mix composition. When the composition and the method of the present invention are so constituted and/or administered, the food-grade acid employed is preferably citric acid, ascorbic acid, tartaric acid, or malic acid, which provides a tasty and palatable flavor while at the same time providing effectiveness for extending the time for gelation of the resulting mix upon the addition of or to water.

In another preferred embodiment according to the present invention, an orally-ingestible non-toxic mineral salt capable of dissolution in the gastric fluids is also administered simultaneously with the active ingredients, namely, niacin and guar gum, preferably in a combination composition therewith and, when the active ingredients according to the present invention are so constituted or administered, the orally-ingestible non-toxic mineral salt capable of dissolution in the gastric fluids assists with more rapid and complete internal dispersion of the guar gum in the gastrointestinal tract, and is preferably selected from the group consisting of calcium carbonate, magnesium carbonate, and potassium carbonate.

It is therefore seen that the present invention provides an oral antihyperlipidemic composition of nicotinic acid (niacin) characterized by reduced and related flushing effects comprising as active ingredients nicotinic acid and guar gum, which is effective in lowering of cholesterol levels, especially LDL cholesterol levels, without the usual undesirable flushing, itching, and related side effects of niacin, and a method of lowering cholesterol levels by employment of such an oral pharmaceutical or dietary supplement composition, or by the simultaneous oral administration of the active ingredients thereof, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. An oral antihyperlipidemic composition of nicotinic acid, having a reduced flushing effect, comprising an effective antihyperlipidemic amount of nicotinic acid and an effective cutaneous-flushingreducing amount of guar gum.

2. A composition of claim 1 wherein the composition contains at least about 50 mg of nicotinic acid.

3. A composition of claim 1 wherein the amount of guar gum is at least about 250 mg.

4. A composition of claim 2 wherein the amount of guar gum is at least about 400 mg, in capsule or tablet form.

5. A composition of claim 2 wherein the amount of guar gum is at least about 400 mg, and an antacid.

6. A composition of claim 4 comprising also a physiologically-acceptable magnesium salt.

7. A composition of claim 4 comprising also an orally-ingestible non-toxic mineral salt capable of dissolution in the gastric fluids.

8. A composition of claim 7, wherein the mineral salt is selected from the group consisting of calcium carbonate, magnesium carbonate, and potassium carbonate.

9. A composition of claim 1, wherein the active ingredients are in granular form and comprising also a quantity of a food-grade acid in powder form which is effective in extending the time for gelation of the resulting mix upon addition of water.

10. A composition of claim 9, wherein the food-grade acid is selected from the group consisting of citric acid, ascorbic acid, tartaric acid, and malic acid.

11. A composition of claim 8 comprising
about 400–500 mg guar gum
about 80–100 mg nicotinic acid
about 80–100 mg magnesium carbonate.

12. A method of combating hyperlipidemia in a subject in need of the same using nicotinic acid, characterized by reduced flushing effect, consisting essentially of the step of simultaneously administering orally to the said subject an effective antihyperlipidemic amount of nicotinic acid and an effective cutaneous-flushing-reducing amount of guar gum.

13. Method of claim 12 comprising the step of administering orally to the said subject both nicotinic acid and guar gum, in the form of a pharmaceutical composition containing both active ingredients.

14. Method of claim 13 wherein the active consisting essentially of ingredients are in capsule or tablet form.

15. Method of claim 14 wherein said method also comprises administration of a physiologically-acceptable mineral salt.

16. Method of claim 13, wherein a single dose comprises about 300–500 mg of niacin and about 1.5–2.5 g of guar gum.

17. Method of claim 15, wherein a single dose comprises about 300–500 mg niacin, about 1.5–2.5 g of guar gum, and about 300–500 mg of a physiologicallyacceptable magnesium salt.

18. Method of claim 12 wherein a dosage unit comprises at least about 250 mg guar gum and at least about 50 mg niacin.

19. Method of claim 16 wherein a single dose comprises at least about 2 g guar gum and at least about 350 mg of niacin.

20. Method of claim 15 wherein a daily dose comprises at least about 6 g guar gum, at least about 1 g niacin, and at least about 1 g magnesium carbonate.

21. Method of claim 12, wherein an orally-ingestible non-toxic mineral salt capable of dissolution in the gastric fluid is simultaneously orally administered.

22. Method of claim 21 wherein the non-toxic mineral salt is a physiologically acceptable magnesium salt.

23. Method of claim 22 wherein the physiologicallyacceptable magnesium salt is magnesium carbonate.

24. Method of claim 12, wherein the active ingredients are in granular form and wherein a quantity of a foodgrade acid also in powder form which is effective in extending the time for gelation of the resulting mix upon addition of water is also concurrently or simultaneously orally administered.

25. Method of claim 21, wherein the mineral salt is selected from the group consisting of calcium carbonate, magnesium carbonate, and potassium carbonate.

26. Method of claim 15, wherein the salt is a physiologically-acceptable magnesium salt.

27. Method of claim 24, wherein the food-grade acid is an organic acid selected from the group consisting of citric acid, ascorbic acid, tartaric acid, and malic acid.

28. A composition of claim 1, wherein the ratio of guar gum by weight to nicotinic acid by weight is at least 3:1.

29. Method of claim 12, wherein the ratio of guar gum by weight to nicotinic acid by weight is at least 3:1.

30. A composition of claim 28, wherein the ratio of guar gum by weight to nicotinic acid by weight is about 3:1 to about 8.3:1.

31. Method of claim 29, wherein the ratio of guar gum by weight to nicotinic acid by weight is about 3:1 to about 8.3:1.

* * * * *

UNITED STATES PATENT AND TRADEMARK OFFICE
CERTIFICATE OF CORRECTION

PATENT NO. : 4,965,252

DATED : Oct. 23, 1990

INVENTOR(S) : Eric H. Kuhrts

It is certified that error appears in the above-identified patent and that said Letters Patent is hereby corrected as shown below:

Title Page, "[56] References Cited" before "PUBLICATIONS" insert
-- U. S. PATENT DOCUMENTS

| | | | |
|---|---|---|---|
| 3,843,778 | 10/1974 | Diamond, et al | 514/819 |
| 4,166,902 | 9/1979 | Ferruti, et al | |
| 4,237,118 | 12/1980 | Howard | 424/140 |
| 4,764,374 | 8/1988 | Grimberg --. | 514/54 |

Column 2, line 21; "acidbinding" should read -- acid-binding --.

Column 2, line 34; "acidsequestering" should read
   -- acid-sequestering --.

Column 2, line 50; "cholesterollowering" should read
   -- cholesterol-lowering --.

Column 3, line 11/12; "inactiviting" should read -- inactivating --.

Column 3, line 19; "doublebarrel" should read -- double-barrel --.

Column 3, line 53; "cholesterollowering" should read
   -- cholesterol-lowering --.

Column 4, line 41; "t good-health" should read -- to good-health --.

Column 5, line 42; "orallyingestible" should read -- orally-ingestible --.

Column 5, line 44/45; "physiologicallyacceptable" should read
   -- physiologically-acceptable --.

UNITED STATES PATENT AND TRADEMARK OFFICE
CERTIFICATE OF CORRECTION

PATENT NO. : 4,965,252

DATED : Oct. 23, 1990

INVENTOR(S) : Eric H. Kuhrts

It is certified that error appears in the above-identified patent and that said Letters Patent is hereby corrected as shown below:

Column 5, line 46/47; "physiologicallyacceptable" should read
-- physiologically-acceptable --.

Column 8, line 35; "No. as" should read -- No. 1 as --.

Column 9, line 16/17; "antihyperipidemic" should read
-- antihyperlipidemic --.

Column 10, line 35; "cutaneous-flushingreducing" should read
-- cutaneous-flushing-reducing --.

Column 11, line 10/11; delete "consisting essentially of".

Column 11, line 22/23; "physiologicallyacceptable" should read
-- physiologically-acceptable --.

Column 12, line 6/7; "physiologicallyacceptable" should read
-- physiologically-acceptable --.

Column 12, line 10; "foodgrade" should read -- food-grade --.

Signed and Sealed this

Seventh Day of April, 1992

Attest:

HARRY F. MANBECK, JR.

*Attesting Officer*        Commissioner of Patents and Trademarks